United States Patent
Hammill et al.

(10) Patent No.: US 7,904,174 B2
(45) Date of Patent: Mar. 8, 2011

(54) IMPLANTABLE LEADS PERMITTING FUNCTIONAL STATUS MONITORING

(75) Inventors: Eric Hammill, Lauderdale, MN (US); Yongxing Zhang, Little Canada, MN (US); Jeffrey P. Bodner, Roseville, MN (US); Paul E. Zarembo, Vadnais Heights, MN (US); Mohan Krishnan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 935 days.

(21) Appl. No.: 10/698,843

(22) Filed: Oct. 31, 2003

(65) Prior Publication Data

US 2005/0096719 A1    May 5, 2005

(51) Int. Cl.
*A61N 1/05* (2006.01)

(52) U.S. Cl. ............... 607/116; 607/119; 607/122

(58) Field of Classification Search .......... 607/119, 607/125, 121–123
See application file for complete search history.

(56) References Cited

U.S. PATENT DOCUMENTS

| 4,559,951 | A | * | 12/1985 | Dahl et al. ............... 600/374 |
| 4,958,632 | A | | 9/1990 | Duggan ............... 128/419 PG |
| 5,201,865 | A | | 4/1993 | Kuehn ............... 607/8 |
| 5,246,438 | A | * | 9/1993 | Langberg ............... 606/33 |
| 5,513,644 | A | | 5/1996 | McClure et al. ............... 128/708 |
| 5,569,220 | A | * | 10/1996 | Webster, Jr. ............... 604/527 |
| 5,824,030 | A | * | 10/1998 | Yang et al. ............... 607/122 |
| 5,944,746 | A | | 8/1999 | Kroll ............... 607/27 |
| 6,253,111 | B1 | * | 6/2001 | Carner ............... 607/122 |
| 6,285,910 | B1 | * | 9/2001 | Verness et al. ............... 607/122 |
| 6,295,476 | B1 | | 9/2001 | Schaenzer ............... 607/122 |
| 6,317,633 | B1 | | 11/2001 | Jorgenson et al. ............... 607/28 |
| 6,405,087 | B1 | | 6/2002 | Snell ............... 607/27 |
| 6,564,107 | B1 | | 5/2003 | Bodner et al. |
| 6,754,531 | B1 | | 6/2004 | Kroll et al. ............... 607/14 |
| 2002/0058981 | A1 | * | 5/2002 | Zhu et al. ............... 607/122 |
| 2002/0099430 | A1 | * | 7/2002 | Verness ............... 607/122 |
| 2002/0120307 | A1 | | 8/2002 | Jorgenson et al. ............... 607/27 |
| 2004/0024424 | A1 | | 2/2004 | Propp et al. ............... 607/27 |
| 2004/0064161 | A1 | | 4/2004 | Gunderson et al. ............... 607/28 |
| 2004/0162593 | A1 | | 8/2004 | Jorgenson et al. ............... 607/27 |

* cited by examiner

*Primary Examiner* — Niketa I Patel
*Assistant Examiner* — Joseph Stoklosa
(74) *Attorney, Agent, or Firm* — Faegre & Benson LLP

(57) ABSTRACT

An implantable lead assembly includes a lead body extending from a proximal end to a distal end having an intermediate portion therebetween, where the lead body includes an insulating layer. A conductor is disposed within the insulating layer and the insulating layer surrounds the conductor. An electrode is coupled to the lead body, and the electrode is in electrical communication with the conductor. At least one conductive sleeve is disposed within the insulating layer. The at least one conductive sleeve surrounds the conductor and is electrically isolated from the electrode. The at least one conductive sleeve has a first impedance value in a first condition.

22 Claims, 6 Drawing Sheets

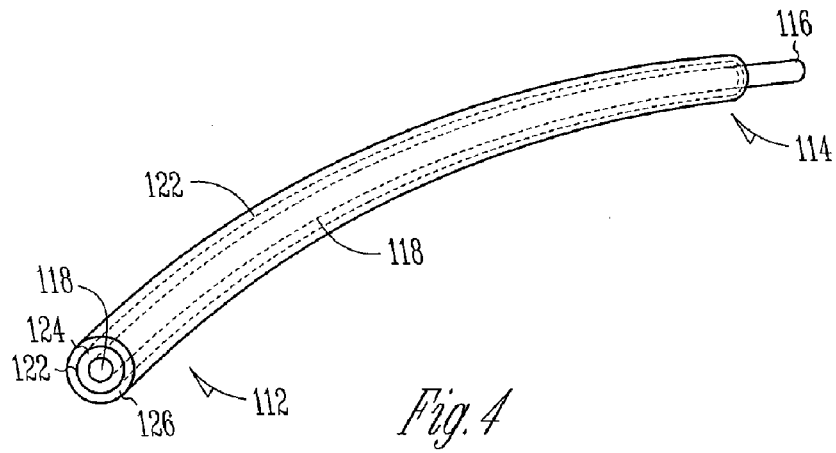
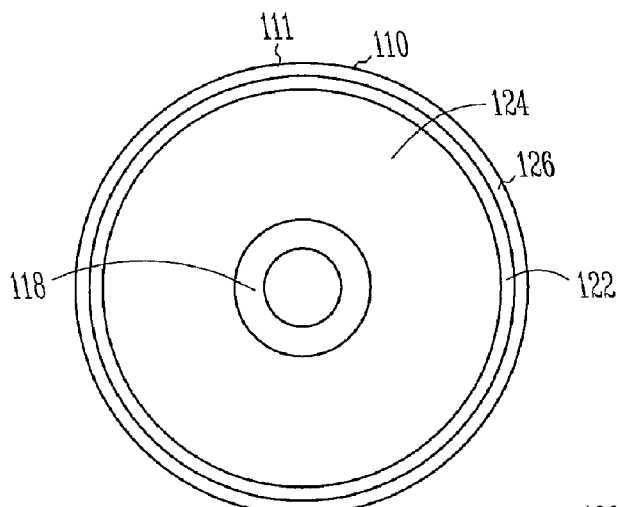
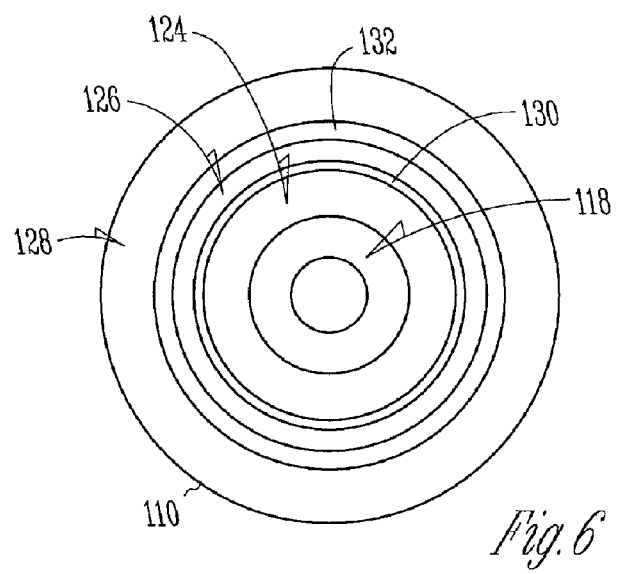

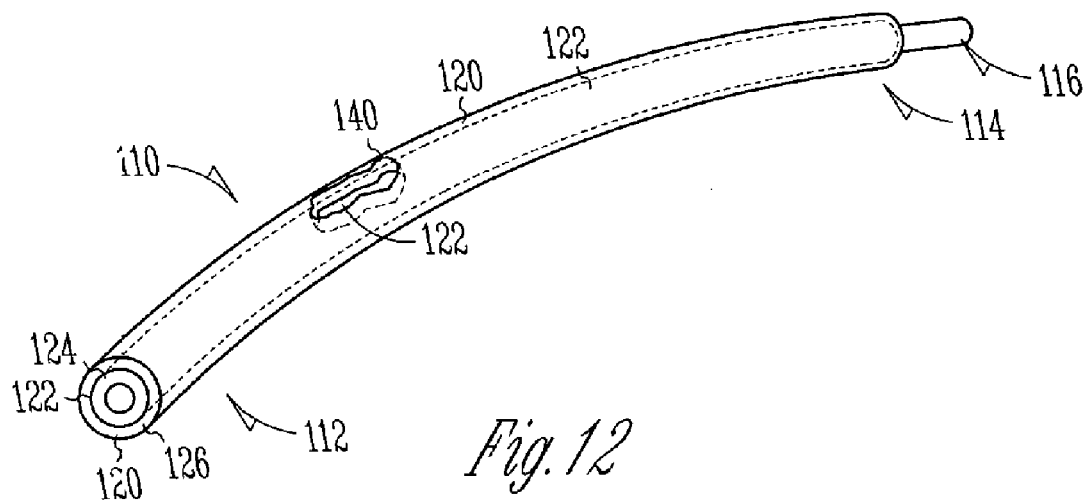

Fig. 12

```
200
         ┌─────────────────────────────────────────────┐ 202
         │   MEASURE FIRST IMPEDANCE OF AT LEAST ONE   │
         │       CONDUCTIVE ELEMENT AT FIRST TIME      │
         └─────────────────────────────────────────────┘
                               │
                               ▼
         ┌─────────────────────────────────────────────┐ 204
         │  MEASURE SECOND IMPEDANCE OF THE AT LEAST ONE │
         │      CONDUCTIVE ELEMENT AT SECOND TIME      │
         └─────────────────────────────────────────────┘
                               │
                               ▼
         ┌─────────────────────────────────────────────┐ 206
         │   SEND SIGNAL IF SECOND IMPEDANCE IS WITHIN A │
         │             PREDETERMINED RANGE             │
         └─────────────────────────────────────────────┘
```

Fig. 13

IMPLANTABLE LEADS PERMITTING FUNCTIONAL STATUS MONITORING

TECHNICAL FIELD

The present invention relates generally to an implantable lead assembly that allows status monitoring of implantable leads.

BACKGROUND

Implantable leads are a critical component in medical device applications. In any implantable medical device (IMD) application, and particularly in pacemaker or implantable cardiac defibrillator applications, it is important to be able to monitor and report the performance and functional status of leads. In some IMD applications, the lead status is monitored for malfunctions, for example, when the lead fractures and is unable to perform.

In one example, the impedance of a lead conductor coupled with an electrode is measured to monitor the status of a lead as described in U.S. Pat. No. 4,958,632. Exposure of the lead to the surrounding environment of the body or fracture of the lead causes measurable changes in the conductor impedance, which signals that the lead has malfunctioned or is beginning to fail. However, conventional lead status monitoring techniques are not able to detect breaches of the lead insulation until the lead conductor impedance changes, which occurs only when the lead has begun to malfunction. In other words, the techniques are only able to detect failure of the lead as the lead conductor begins to fail.

U.S. Pat. No. 6,317,633, is another example of lead conductor monitoring through impedance measurements. However, the system does not address the issue that the lead conductor impedance only changes upon onset of failure in the lead conductor, and not before, when only the insulation has been partially breached and the lead is still fully functional.

What is needed are implantable leads that overcome the shortcomings of previous implantable leads. What is further needed are implantable leads that permit functional status monitoring of lead insulation before the onset of lead conductor failure, which would allow replacement of a lead before degradation in performance.

SUMMARY

An implantable lead assembly includes a lead body extending from a proximal end to a distal end, the lead body includes an insulating layer. A conductor is disposed within the insulating layer, and the insulating layer surrounds the conductor. An electrode is coupled to the lead body, the electrode is in electrical communication with the conductor. At least one conductive sleeve is disposed within the insulating layer. The at least one conductive sleeve surrounds the conductor and is electrically isolated from the electrode. The at least one conductive sleeve has a first impedance value in a first condition.

Several options for the implantable lead assembly follow. In one option, the at least one conductive sleeve is exposed to a surrounding environment in a second condition and the at least one conductive sleeve has a second impedance value that is within a predetermined range. In another option, a second conductive sleeve is disposed within the insulating layer and is electrically isolated from the electrode. In yet another option, the second conductive sleeve surrounds the conductor and the at least one conductive sleeve. In still another option, a second conductor is disposed within the insulating layer, and the second conductive sleeve surrounds the second conductor.

In another embodiment, a method comprises measuring a first impedance of an at least one conductive sleeve at a first time in an implantable lead assembly. The implantable lead assembly includes a lead body having a conductor disposed therein and an electrode coupled to the lead body. The electrode is in electrical communication with the conductor. An insulating layer surrounds the conductor and at least one conductive sleeve is disposed within the insulating layer. The conductive sleeve surrounds the conductor. The method further includes measuring a second impedance of the at least one conductive sleeve at a second time. Additionally, the method includes sending a signal if the second impedance is within a predetermined range.

Several options for the method follow. In one option, the method includes comparing the first impedance with the second impedance. The method includes coupling the implantable lead assembly to a pulse generator, in another option. The pulse generator is in electrical communication with the conductive sleeve in one option. In another option, measuring the first impedance and the second impedance are performed by a pulse generator. In still another option, the method further includes coupling a monitoring unit to a terminal disposed on the lead body. The monitoring unit is in electrical communication with the conductive sleeve in one option. In a further option, measuring the first impedance and measuring the second impedance are performed by the monitoring unit.

The implantable lead assembly allows for detection of breaches in lead insulation before malfunction of a lead conductor. With the above described design, exposure of the conductive sleeve to a surrounding environment through wear of the lead insulation measurably changes the impedance of the conductive sleeve. This measurable change of impedance signals wear of the lead insulation before the lead conductor itself is exposed to the surrounding environment. In other words, the implantable lead assembly detects wear of lead insulation before the lead conductor can malfunction or fail thus preventing a potential tragedy for a patient. Notification of lead insulation wear allows the implantable lead assembly to be safely replaced before failure of the lead. Furthermore, impedance measurements can be safely and easily performed by pulse generators (e.g., pacemakers), which can also alert a patient that the implantable lead assembly needs replacement. Additionally, a pulse generator can measure impedance at a variety of preprogrammed times, intermittently, or continuously, and also store the readings for later use by a physician. Further still, a separate monitoring unit can be attached to the implantable lead assembly to take impedance measurements as well.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 4 is a perspective view of an implantable lead assembly constructed in accordance with another embodiment.

FIG. 5 is a cross-sectional view of an implantable lead assembly constructed in accordance with one embodiment.

FIG. 6 is a cross-sectional view of an implantable lead assembly constructed in accordance with another embodiment.

FIG. 12 is a perspective view of an implantable lead assembly constructed in accordance with another embodiment showing wear.

FIG. 13 is a block diagram illustrating one embodiment of a method of use for the implantable lead assembly.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the subject matter of this application is defined by the appended claims and their equivalents.

Figure 1:
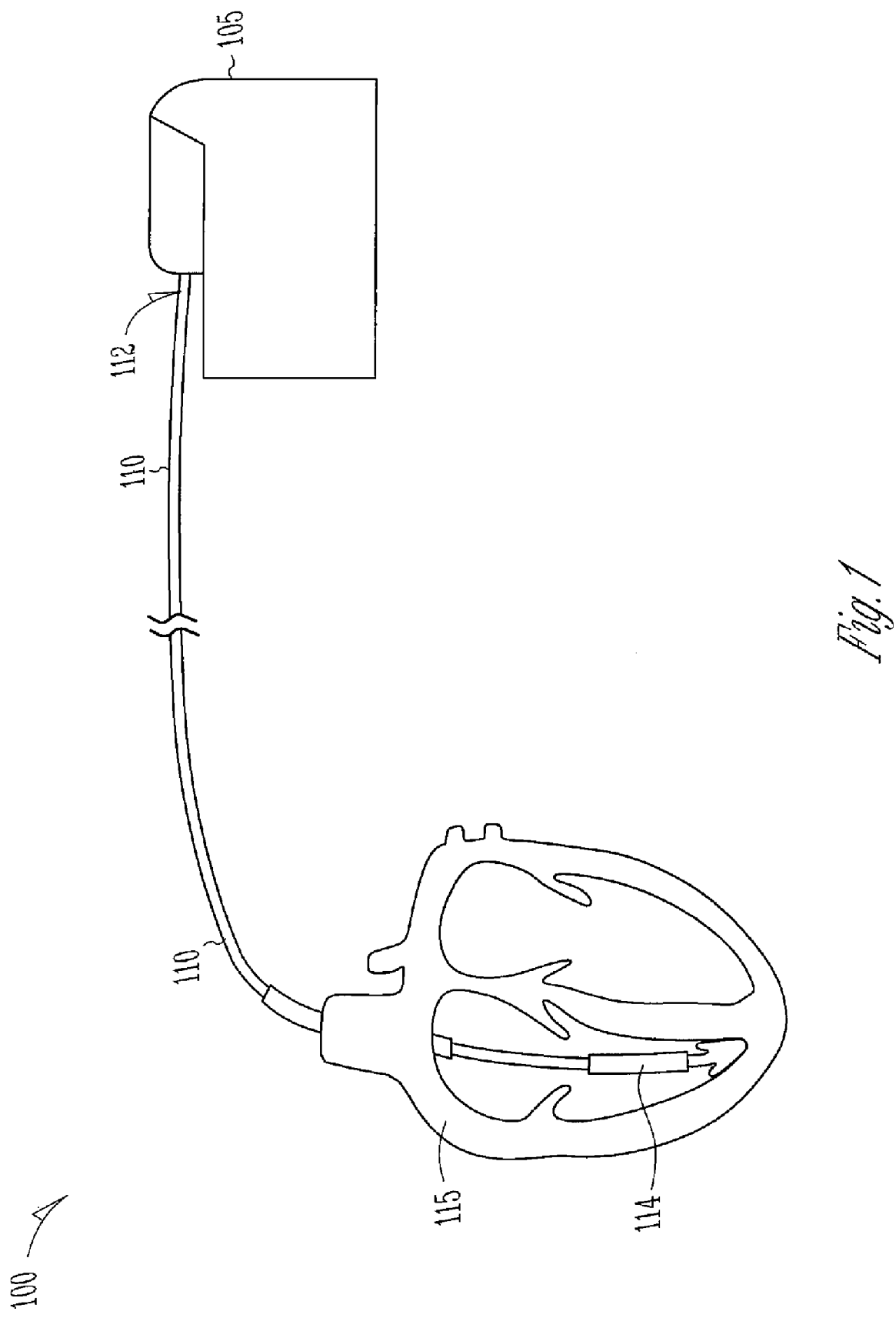
FIG. 1 is a block diagram of a system with a lead for use with a heart and constructed in accordance with one embodiment.

FIG. 1 is a block diagram of a system 100 for delivering and/or receiving electrical pulses or signals to stimulate and/or sense the heart. The system for delivering pulses 100 includes a pulse generator 105 and an implantable lead assembly 110. The pulse generator 105 includes a source of power as well as an electronic circuitry portion. The pulse generator 105 is a battery-powered device which generates a series of timed electrical discharges or pulses used to initiate depolarization of excitable cardiac tissue. The pulse generator 105 is generally implanted into a subcutaneous pocket made in the wall of the chest. Alternatively, the pulse generator 105 is placed in a subcutaneous pocket made in the abdomen, or in other locations.

Figure 2:
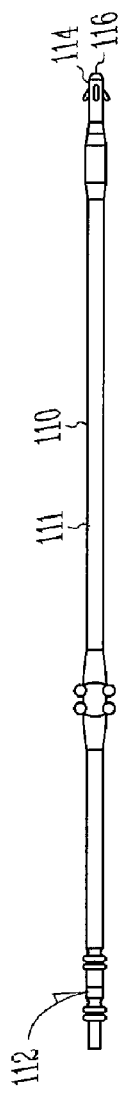
FIG. 2 is a side view of an implantable lead assembly constructed in accordance with one embodiment.
Figure 3:
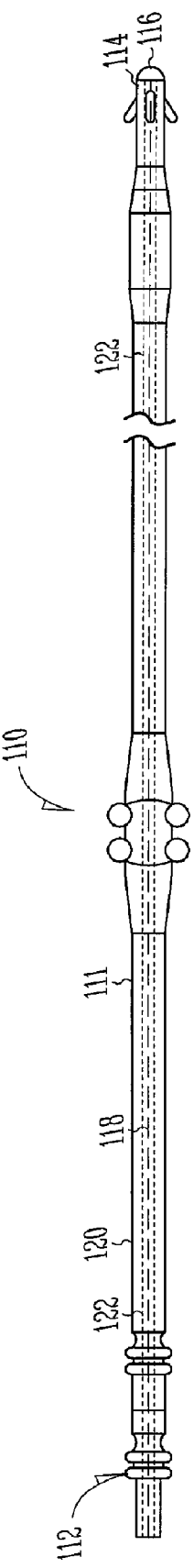
FIG. 3 is an enlarged side view of an implantable lead assembly constructed in accordance with one embodiment.
Figure 8:
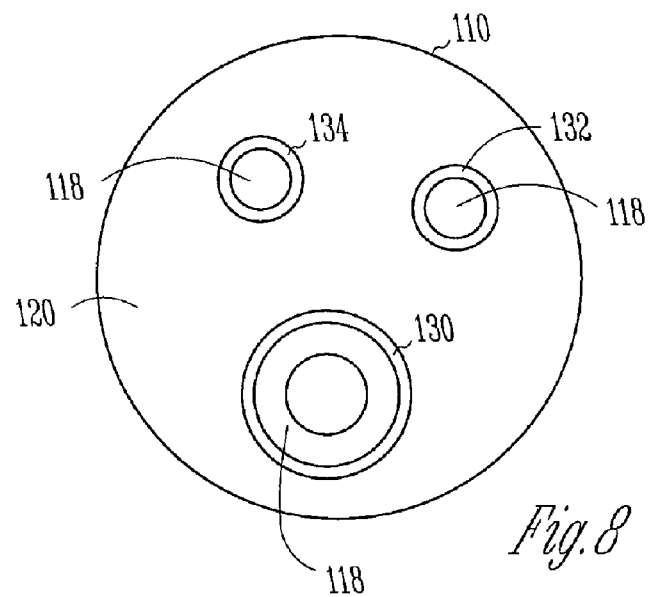
FIG. 8 is a cross-sectional view of an implantable lead assembly constructed in accordance with still yet another embodiment.

The implantable lead assembly 110, shown in more detail in FIG. 2, has a lead body 111 extending from a proximal end 112, where it is coupled with the pulse generator 105, and extending through an intermediate portion to a distal end 114, which is coupled with a portion of a heart 115, in the implanted condition (one example is shown in FIG. 1). In another example, the lead body distal end 114 is disposed adjacent to the heart 115, in the implanted condition. The distal end 114 of the implantable lead assembly 110 includes at least one electrode 116 which electrically couples the implantable lead assembly 110 with the heart 115. In one option, the electrode 116 is coupled with the lead body 111. The electrode 116, in one option, is either a unipolar or multipolar type electrode. In another option, multiple electrodes are provided. At least one electrical conductor 118, as shown in phantom lines in FIG. 3, is disposed within the implantable lead assembly 110 and electrically couples the electrode 116 with the proximal end 112 of the implantable lead assembly 110. The electrical conductor 118 carries electrical current and pulses between the pulse generator 105 and the electrode 116 located in the distal end 114 of the implantable lead assembly 110. In yet another option, multiple electrical conductors 118 are disposed within the implantable lead assembly 110, as shown in FIG. 8.

The lead body 111, in one option, includes an insulating layer 120 formed of a biocompatible polymer suitable for implementation within the human body. The insulating layer 120 is made from a silicone rubber type polymer, in one option. In another option, the insulating layer 120 includes polyurethane. In yet another option, the insulating layer 120 includes polytetrafluoro-ethylene (PTFE). In still another option, the insulating layer 120 includes ethylene-tetrafluoroethylene (ETFE), or polysiloxane urethane. The insulating layer 120 surrounds the electrical conductor 118. The implantable lead assembly 110 travels from the pulse generator 105 and into a major vein. The distal end 114 of the implantable lead assembly 110, in one option, is placed inside or adjacent to the heart 115. In another option, the distal end 114 of the implantable lead assembly 110 is placed, or "floats," inside a vein or within a chamber of the heart 115.

As shown in FIGS. 3 and 4 in phantom lines, a conductive sleeve 122 is disposed within the insulating layer 120, in one option. The conductor 118 is disposed within the conductive sleeve 122, so the conductive sleeve 122 surrounds the conductor 118. In other words, the conductive sleeve 122 defines a perimeter around the conductor 118. In one option, the conductive sleeve 122 is comprised of discrete conductive elements and defines a broken perimeter around the conductor 118. Optionally, the conductive sleeve 122 is aligned with a longitudinal axis defined by the conductor 118. The conductive sleeve 122 is electrically isolated from the electrode 116 and conductor 118 by the insulating layer 120. In another option, the insulating layer 120 also surrounds the conductive sleeve 122, thereby isolating the conductive sleeve from a surrounding environment (for example bodily fluids). When surrounded by the insulating layer 120, the conductive sleeve 122 has a first impedance value in a non-breached first condition. In one option, the conductive sleeve 122 is in an open circuit when isolated from the surrounding environment and has an infinite first impedance value. In another option, shown in FIG. 4, the insulating layer 120 (FIG. 3) includes a first insulating portion 124 interposed between the conductor 118 and the conductive sleeve 122, and a second insulating portion 126 that surrounds the conductive sleeve 122. In still another option, the conductive sleeve 122 is exposed to a surrounding environment in a breached second condition as described below. Optionally, the conductive sleeve 122 extends from the proximal end of the implantable lead body 111 (FIG. 3) along substantially one third of the lead body length, where a large amount of wear is likely to occur.

In one option, the conductive sleeve 122 is a thin coating of conductive material applied to an insulating layer so as to surround the insulating layer and the conductor 118 disposed therein. The coating of conductive material, in one option, is metallic and is applied by sputtering or vapor deposition. In another option, the conductive sleeve 122 is a conductive polymer. A conductive polymer is applied to the implantable lead assembly 110 (FIG. 3) by dipping the implantable lead assembly in a conductive polymer monomer solution, in one option. Optionally, the polymer is applied by plasma polymerization of an electrically conductive polymer on to the implantable lead assembly 110. In another option, the polymer includes conductive additives, for example, graphite, silver or platinum. In yet another option, the polymer itself is intrinsically conductive. In still another option, the conductive sleeve 122 includes a shape memory alloy formed into a tubular shape by extrusion, or by rolling or coiling of thin alloy films into a tube. In a further option, the implantable lead assembly 110 is created with alternating layers of polymer, where metallic fillers are added to the polymer at various layers to create the conductive sleeve 122.

As shown in FIG. 5, in one option, the conductive sleeve 122 is disposed substantially adjacent to the outer surface of the lead body 111. The conductive sleeve 122 surrounds the first insulating portion 124 and conductor 118 so as to define a perimeter around the conductor, as described above. The first insulating layer includes silicone, in one option. The conductive sleeve 122 is interposed between the first insulating portion 124 and the second insulating portion 126, thereby electrically isolating the conductive sleeve 122 from the electrode 116 (FIG. 4) and conductor 118. The second insulating portion 126 includes polyurethane, in another option. In yet another option, the conductor 118 is coated with a thin insulating layer of ETFE, which is interposed between the conductor 118 and the first insulating portion 124.

Figure 7:
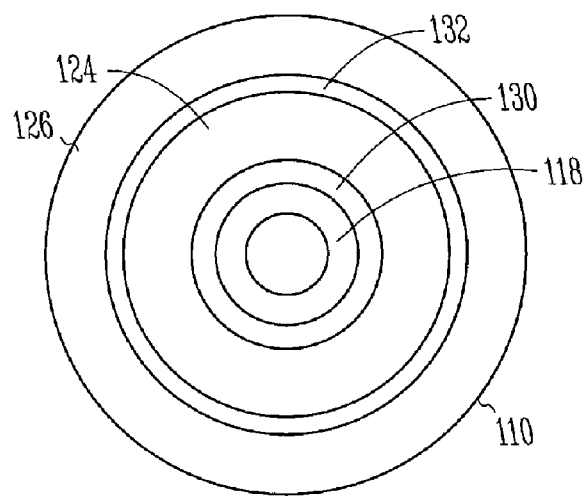
FIG. 7 is a cross-sectional view of an implantable lead assembly constructed in accordance with yet another embodiment.

In another option, as shown in FIGS. 6 and 7, multiple conductive sleeves are disposed within the implantable lead assembly 110. As shown in FIG. 6, the insulating layer includes a first insulating portion 124, second insulating portion 126 and third insulating portion 128. The first insulating portion 124 surrounds the electrical conductor 118. The second insulating portion 126 is disposed around and surrounds the first insulating portion 124. A first conductive sleeve 130 is interposed between the first insulating portion 124 and second insulating portion 126. The first conductive sleeve 130 surrounds the conductor 118 so as to substantially define a perimeter. The third insulating portion 128 surrounds the second insulating portion 126, and a second conductive sleeve 132 is interposed between the second insulating portion and the third insulating portion. Like the first conductive sleeve 130, the second conductive sleeve 132 is electrically isolated from the electrode 116 and conductor 118. In one option, the second conductive sleeve 132 surrounds the conductor 118 and first conductive sleeve 130, substantially defining a perimeter around both structures. In another option, the first insulating portion 124, second insulating portion 126 and third insulating portion 128 include different insulating materials as described above with respect to insulating layer 120. In still another option, the first insulating portion 124, second insulating portion 126, and third insulating portion 128 include substantially similar insulating materials.

Referring specifically to FIG. 7, in one option, the first conductive sleeve 130 surrounds the conductor 118 and is adjacent thereto. A thin insulating layer of ETFE, PTFE, or other insulating material is interposed between the conductor 118 and first conductive sleeve 130, thus isolating the conductor from electrical communication with the first conductive sleeve, in another option. Because the first conductive sleeve 130 surrounds the conductor 118, the first conductive sleeve substantially defines a perimeter around the conductor, as described above. A first insulating portion 124 surrounds the first conductive sleeve 130. A second insulating portion 126 surrounds the first insulating portion 124. The second conductive sleeve 132 is interposed between the first insulating portion 124 and the second insulating portion 126. The second conductive sleeve 132 surrounds the conductor 118 and first conductive sleeve 130 so as to substantially define a perimeter around the conductor and first conductive sleeve. In one option, the first insulating portion 124 and second insulating portion 126 include different insulating materials, as was described above, with respect to insulating layer 120. In still another option, the first insulating portion 124 and second insulating portion 126 include substantially similar insulating materials.

Referring now to FIG. 8, implantable lead assembly 110 is shown with multiple conductors 118 and corresponding multiple conductive sleeves 130, 132, 134 disposed therein. The first conductive sleeve 130 surrounds a conductor 118, in one option. The conductor 118 is coated with a thin insulating layer of ETFE, PTFE or other insulating material to electrically isolate the conductor 118 from the first conductive sleeve 130. In another option, the second conductive sleeve 132 surrounds another conductor 118. As discussed above, the conductor 118 is coated is thereby electrically isolated from the conductor 118. A third conductive sleeve 134 surrounds an additional conductor 118, in yet another option. The conductor 118 is also coated with a thin insulating layer of ETFE or PTFE to electrically isolate the third conductive sleeve 134 from the conductor 118. In one option, the conductors 118 and conductive sleeves 130, 132, 134 are disposed within insulating layer 120 of implantable lead assembly 110. As described above, in one option, each conductive sleeve 130, 132, 134 is disposed adjacently to a conductor 118. In another option however, each conductive sleeve 130, 132, 134 is offset from the respective conductor 118. In this option, the conductive sleeves 130, 132, 134 are disposed within the insulating layer 120, but still otherwise surround the respective conductors 118. Optionally, one or two of the conductive sleeves 130, 132, 134 is offset from the respective conductor 118, while the remaining conductive sleeves are adjacent the respective conductor. In still another option, one or more than one of conductive sleeves 130, 132 and/or 134 surrounds multiple conductors 118. In a further option, the conductors 118 extend parallel to the longitudinal axis of the implantable lead assembly 110 as do the conductive sleeves 130, 132, 134. As the conductive sleeves 130, 132, 134 surround the respective conductors 118, each conductive sleeve substantially defines a perimeter around the respective conductor, as described in the above embodiments.

Figure 9:
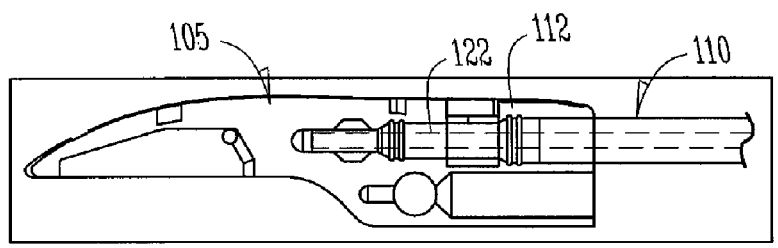
FIG. 9 is a side view of an implantable lead assembly constructed in accordance with one embodiment with a portion of a pulse generator.

As shown in FIGS. 1 and 9, in one option, the conductive sleeve 122 is coupled to the pulse generator 105 when the proximal end 112 of the implantable lead assembly 110 is coupled with the pulse generator 105. In another option, the pulse generator 105 is operable to measure the impedance value of the conductive sleeve 122. In other words, the conductive sleeve 122 is in electrical communication with the pulse generator 105, permitting impedance measurement by the pulse generator.

Figure 10:
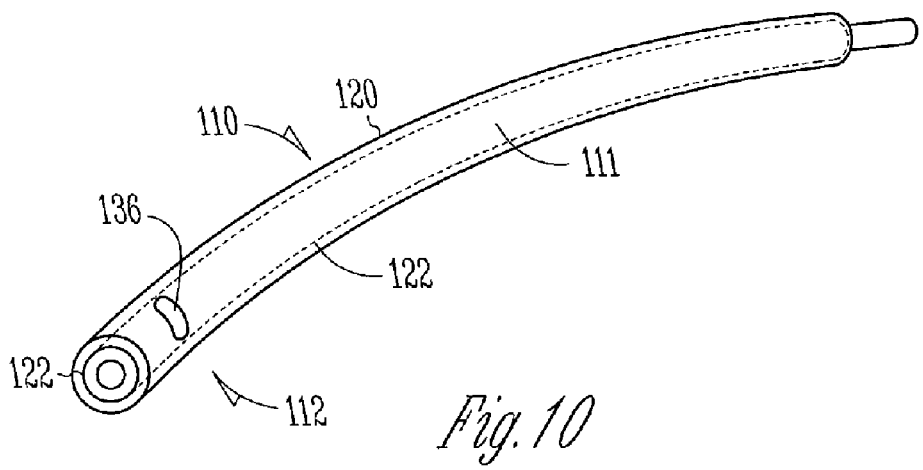
FIG. 10 is a perspective view of an implantable lead assembly constructed in accordance with yet another embodiment.
Figure 11:
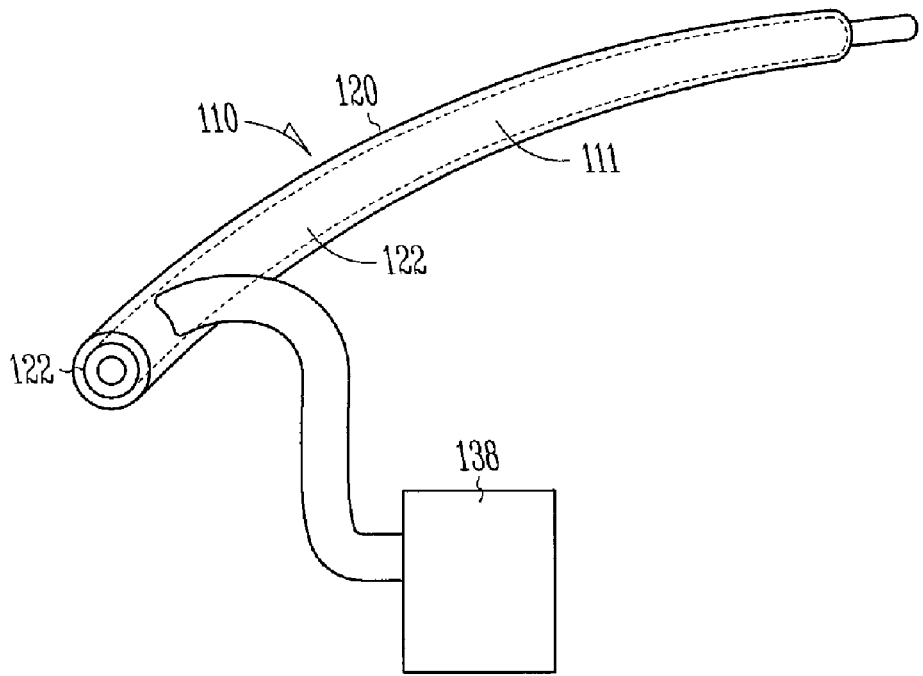
FIG. 11 is a perspective view of an implantable lead assembly constructed in accordance with yet another embodiment along with a monitoring unit.

Referring now to FIGS. 10 and 11, in one option, the implantable lead assembly 110 includes a terminal 136 disposed on the outer surface of the lead body 111. In another option, the terminal 136 extends from the outer surface of the lead body 111, through insulating layer 120, to the conductive sleeve 122. The terminal 136 is in electrical communication with the conductive sleeve 122, in yet another option. In a further option, when needed (as described below), a monitoring unit 138 (FIG. 11) is coupled to the implantable lead assembly 110, specifically the terminal 136, and is in electrical communication with the terminal 136. The monitoring unit 138 is also in electrical communication with the conductive sleeve 122 through the terminal 136. In still another option, the monitoring unit 138 is operable to measure the impedance value of the conductive sleeve 122. Optionally, the monitoring unit 138 is implanted with the pulse generator 105 (FIG. 1) and implantable lead assembly 110. In another option, the monitoring unit 138 is disposed outside the body, and a cable couples the monitoring unit to the terminal 136 of implantable lead assembly 110. In one option, the monitoring unit 138 and pulse generator 105 both measure impedance of the conductive sleeve 122. In another option, only the monitoring unit 138 measures the impedance of the conductive sleeve 122. In yet another option, the monitoring unit 138 measures and records the impedance of conductive sleeve 122.

As shown in FIG. 1, in operation, the implantable lead assembly 110 is coupled to the pulse generator 105. The electrode 116 of the implantable lead assembly 110 is electrically coupled with the heart 115. As described above, the pulse generator 105 is operable to measure the impedance of the conductive sleeve 122, in one option. In another option, the pulse generator 105 is operable to measure the impedance of the conductive sleeves 130, 132, 134 (FIGS. 5, 6 and 7). When desired, the impedance of the conductive sleeve 122 is measured at a first time by the pulse generator 105. The conductive sleeve 122 impedance is measured at a later measurement is compared against the first impedance measurement by the pulse generator. A change of impedance to within a predetermined range is indicative of wear of the insulating layer 120 of the implantable lead assembly 110. In other words, if wear has ablated the insulating layer 120 and exposed the conductive sleeve 122 to the surrounding environment, the impedance of the conductive sleeve 122 will change from the first impedance value to the second impedance value within a predetermined range. As shown in FIG. 12, wear of the insulating layer 120 creates a breach or opening 140 in the implantable lead assembly 110. As shown in phantom lines in FIG. 12, after sufficient wear, the opening 140 extends from the outer surface of the implantable lead assembly 110 to the conductive sleeve 122. In this second breached condition, the surrounding environment contacts the exposed conductive sleeve 122 and thereby changes the impedance value of the conductive sleeve. A closed circuit is formed between the pulse generator 105, conductive sleeve 122, and the surrounding environment (for example body fluids) which contacts the pulse generator. In one option, the predetermined range of impedance values is less than or equal to about 2000 ohms. If the second impedance value is within the predetermined range, a signal is sent that is capable of alerting a patient or physician, for example, that the implantable lead assembly 110 needs to be replaced. In another option, the second impedance value is compared against the first impedance value and a signal sent if the second impedance value is substantially lower (for example, less than or equal to 2000 ohms) than the first impedance value (for example, an infinite impedance). In still another option, the impedance measurements are stored within the pulse generator 105 for future access by a physician. Optionally, the impedance measurements are taken at preprogrammed times. The pulse generator 105 makes impedance measurements intermittently, in yet another option. Alternatively, the pulse generator 105 measures impedance continuously. In a similar manner, impedance measurements and comparisons therebetween as herein described may be taken with conductive sleeves 130, 132, 134, described in the above embodiments.

Referring again to FIGS. 10 and 11, in operation the implantable lead assembly 110 is coupled with the monitoring unit 138, which is operable to make impedance measurements. The monitoring unit 138 is coupled to the terminal 136 and also in electrical communication thereto, in one option. In another option, the terminal 136 is coupled to the conductive sleeve 122 and in electrical communication thereto. The monitoring unit 138 is thereby in electrical communication with the conductive sleeve 122 through the terminal 136. In still another option, the monitoring unit 138 is operable to measure the impedance of the conductive sleeves 130, 132, 134 (FIGS. 5, 6 and 7). When desired, the impedance of the conductive sleeve 122 is measured at a first time by the monitoring unit 138. The conductive sleeve 122 impedance is measured at a later second time by the monitoring unit 138. As described above, a change of impedance to within a predetermined range is indicative of wear of the insulating layer 120 of the implantable lead assembly 110 and exposure of the conductive sleeve 122 to the surrounding environment. In one option, the predetermined range of impedance values is less than or equal to about 2000 ohms. If the second impedance measurement is within the predetermined range, a signal is sent that is capable of alerting a patient or physician that the implantable lead assembly 110 needs to be replaced. In another option, the second impedance value is compared against the first impedance value and a signal sent if the second impedance value is substantially lower (for example, less than or equal to 2000 ohms) than the first impedance value (for example, an infinite impedance). Optionally, the impedance measurements are stored within the monitoring unit 138 for future access by a physician. In another option, the impedance measurements are taken at preprogrammed times. In yet another option, the monitoring unit 138 makes impedance measurements intermittently. Alternatively, the monitoring unit 138 measures impedance continuously. In a similar manner, impedance measurements and comparisons therebetween as herein described may be taken with conductive sleeves 130, 132, 134.

In another embodiment, a method 200 is shown in FIG. 13, which comprises measuring a first impedance of a conductive sleeve at a first time in an implantable lead assembly, as principally shown in block 202. The implantable lead assembly includes a lead body having a conductor disposed therein, an electrode is coupled to the lead body. The electrode is in electrical communication with the conductor. An insulating layer surrounds the conductor. The conductive sleeve is disposed within the insulating layer and also surrounds the conductor. The method further includes measuring a second impedance of the conductive sleeve at a second time, as shown in block 204. As shown in block 206, the method also includes sending a signal if the second impedance is within a predetermined range. In one option, the predetermined range of impedance values is less than or equal to about 2000 ohms.

Several options for the method follow. For example, in one option, the method further includes comparing the first impedance with the second impedance. In another option, the method further includes wearing away the insulating layer during an intermediate period between the first time and the second time. In still another option, the method includes coupling the implantable lead assembly to a pulse generator, where the pulse generator is in electrical communication with the conductive sleeve. In yet another option, the method further includes measuring the first impedance and second impedance with the pulse generator. The method further includes storing the impedance measurements within the pulse generator, in another option. Additionally, in another option, the method further includes coupling a monitoring unit to a terminal disposed on the lead body, where the terminal is in electrical communication with the conductive sleeve. Optionally, the method includes measuring the first impedance and second impedance of the conductive sleeve with the monitoring unit. In another option, measuring the first impedance and second impedance of the conductive sleeve includes measuring impedance at preprogrammed times. In yet another option, the method includes intermittently measuring impedance of the conductive sleeve. In still another option, the method conversely includes continuously measuring impedance.

The above described design for an implantable lead assembly allows for detection of breaches in lead insulating layers before malfunction of a lead. Exposure of the conductive sleeve to a surrounding environment through wear of the lead insulation measurably changes the impedance of the conductive sleeve. This change of impedance, when within a predetermined range, signals wear of the lead insulation before the lead conductor itself is exposed to the surrounding environment. In other words, the implantable lead assembly detects wear of lead insulation before the lead conductor can malfunction or fail thus preventing a potential tragedy for a patient. Notification of lead insulation wear allows the implantable lead assembly to be safely replaced before failure of the lead.

Furthermore, impedance measurements are safely and easily performed by pulse generators (e.g. pacemakers), which also alert a patient and physician that the implantable lead assembly needs replacement. Additionally, a pulse generator can measure impedance at a variety of preprogrammed times or intermittently, and then also store the readings for later use by a physician. Further still, a separate monitoring unit may be attached to the implantable lead assembly to take impedance measurements as well. The implantable lead assembly and the methods described above may also be used in other implantable medical lead applications beyond cardiac pacemakers, for example neurological recording and stimulation.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An implantable lead assembly comprising:
   a lead body extending from a proximal end to a distal end having an intermediate portion therebetween, wherein the lead body includes an insulating layer;
   a conductor disposed within the insulating layer, wherein the insulating layer surrounds the conductor;
   an electrode coupled to the lead body, wherein the electrode is in electrical communication with the conductor;
   at least one impedance monitoring conductive sleeve disposed within the insulating layer, the at least one impedance monitoring conductive sleeve continuously surrounds the conductor and extends continuously along the conductor from the proximal end to at least the intermediate portion, wherein the at least one impedance monitoring conductive sleeve is physically isolated and electrically isolated from the electrode and the conductor, and the impedance monitoring conductive sleeve is a coating of conductive material; and
   the at least one impedance monitoring conductive sleeve has a first measured impedance value in a first condition, and the at least one impedance monitoring conductive sleeve is adapted for electrical isolation from a lead body exterior environment in the first condition, and the at least one impedance monitoring conductive sleeve has a second measured impedance value less than the first measured impedance value in a second condition with the insulating layer is breached and the at least one impedance monitoring conductive sleeve is in electrical communication with the lead body exterior environment.

2. The implantable lead assembly of claim 1, wherein the at least one impedance monitoring conductive sleeve is adapted for exposure to a lead body exterior environment in a second condition and the at least one impedance monitoring conductive sleeve has a second impedance value, where the second impedance value is within a predetermined range.

3. The implantable lead assembly of claim 1, wherein an opening extends from an outer surface of the insulating layer to the at least one impedance monitoring conductive sleeve to expose the at least one impedance monitoring conductive sleeve to the lead body exterior environment.

4. The implantable lead assembly of claim 1, wherein the at least one impedance monitoring conductive sleeve extends through the lead body, and the at least one impedance monitoring conductive sleeve is substantially aligned with a lead body longitudinal axis.

5. The implantable lead assembly of claim 1, further comprising:
   a second conductive sleeve disposed within the insulating layer, wherein the second conductive sleeve is electrically isolated from the electrode.

6. The implantable lead assembly of claim 5, wherein the second conductive sleeve surrounds the conductor and the at least one conductive sleeve.

7. The implantable lead assembly of claim 6, wherein the insulating layer includes a first portion, a second portion, and a third portion, the at least one impedance monitoring conductive sleeve is interposed between the first portion and the second portion, and the second conductive sleeve is interposed between the second portion and the third portion, the third portion surrounds the second conductive sleeve.

8. The implantable lead assembly of claim 5, further comprising:
   a second conductor, the second conductor disposed within the insulating layer, wherein the second conductive sleeve surrounds the second conductor.

9. The implantable lead assembly of claim 1, further comprising:
   a pulse generator coupled with the implantable lead assembly, wherein the pulse generator is in electrical communication with the at least one conductive sleeve.

10. The implantable lead assembly of claim 9, further comprising:
    a monitoring unit coupled with the implantable lead assembly, wherein the monitoring unit is in electrical communication with the at least one impedance monitoring conductive sleeve.

11. An implantable lead assembly comprising:
    a lead body extending from a proximal end to a distal end having an intermediate portion therebetween, the lead body including a lead body exterior, and the lead body includes an insulating layer;
    a conductor disposed within the insulating layer, wherein the insulating layer surrounds the conductor;
    an electrode coupled to the lead body, wherein the electrode is in electrical communication with the conductor;
    at least one impedance monitoring conductive sleeve interposed between the lead body exterior and the conductor, the at least one impedance monitoring conductive sleeve at least partially surrounds the conductor, the at least one impedance monitoring conductive sleeve continuously extends along the conductor from the proximal end to at least the intermediate portion, wherein the at least one impedance monitoring conductive sleeve is physically isolated and electrically isolated from the electrode and the conductor, and the conductive sleeve is a conductive coating;

the at least one impedance monitoring conductive sleeve has a first measured impedance value in a first condition, and the at least one impedance monitoring conductive sleeve is electrically isolated from a lead body exterior environment in the first condition, and the at least one impedance monitoring conductive sleeve has a second measured impedance value less than the first measured impedance value in a second condition where the insulating layer is breached and the at least one impedance monitoring conductive sleeve is in electrical communication with the lead body exterior environment; and a connector sized and shaped for electrically and mechanically connecting the at least one impedance monitoring conductive sleeve with an impedance monitoring device.

12. The implantable lead assembly of claim 11, and the at least one impedance monitoring conductive sleeve substantially surrounds the conductor.

13. The implantable lead assembly of claim 11, and wherein when the at least one impedance monitoring conductive sleeve is exposed to a lead body exterior environment in a second condition the at least one impedance monitoring conductive sleeve has a second impedance value, where the second impedance value is within a predetermined range.

14. The implantable lead assembly of claim 11, and the at least one impedance monitoring conductive sleeve extends through the lead body, and the at least one impedance monitoring conductive sleeve is substantially aligned with a lead body longitudinal axis.

15. The implantable lead assembly of claim 11, further comprising a second conductive sleeve disposed within the insulating layer, wherein the second conductive sleeve is electrically isolated from the electrode.

16. The implantable lead assembly of claim 15, wherein the second conductive sleeve surrounds the conductor and the at least one impedance monitoring conductive sleeve.

17. The implantable lead assembly of claim 15, further comprising a second conductor, the second conductor disposed within the insulating layer, and the second conductive sleeve surrounds the second conductor.

18. The implantable lead assembly of claim 11, further comprising a pulse generator coupled with the implantable lead assembly, and the pulse generator is in electrical communication with the at least one impedance monitoring conductive sleeve.

19. The implantable lead assembly of claim 18, further comprising a monitoring unit coupled with the implantable lead assembly, and the monitoring unit is in electrical communication with the at least one impedance monitoring conductive sleeve.

20. The implantable lead assembly of claim 1, in a first non-breached condition where the impedance monitoring conductive sleeve is electrically isolated from a lead body exterior environment by the insulating layer a first impedance measurement across the impedance monitoring conductive sleeve and the lead body exterior environment has the first measured impedance value, and in a second breached condition where the impedance monitoring conductive sleeve is exposed to the lead body exterior environment a second impedance measurement across the impedance monitoring conductive sleeve and the lead body exterior environment has the lower second measured impedance value.

21. The implantable lead assembly of claim 1, the impedance monitoring conductive sleeve including an impedance monitoring conductive sleeve connector sized and shaped for connection with an impedance monitoring device.

22. The implantable lead assembly of claim 11, the at least one impedance monitoring conductive sleeve includes a plurality of discrete conductive elements.

* * * * *